(12) United States Patent
Lei et al.

(10) Patent No.: US 8,980,235 B2
(45) Date of Patent: Mar. 17, 2015

(54) COATED METAL PYRITHIONE PARTICLES FOR TREATMENT OF MICROORGANISMS

(75) Inventors: Deqing Lei, Hamden, CT (US); George Polson, Harwington, CT (US); Diana T. Ciccognani, Cheshire, CT (US); Kevin N. DiNicola, Wolcott, CT (US); Richard B. Shalvoy, Cheshire, CT (US); Katherine P. Roberts, Derby, CT (US); Louis L. Punto, Randolph, NJ (US); James Robert Schwartz, West Chester, OH (US); David Joseph Kaufman, Fairfield, OH (US)

(73) Assignees: Arch Chemicals, Inc., Norwalk, CT (US); The Proctor & Gamble Company, Cincinnati, OH (US)

( * ) Notice: Subject to any disclaimer, the term of this patent is extended or adjusted under 35 U.S.C. 154(b) by 1800 days.

(21) Appl. No.: 10/952,337

(22) Filed: Sep. 28, 2004

(65) Prior Publication Data

US 2005/0118276 A1  Jun. 2, 2005

Related U.S. Application Data

(60) Provisional application No. 60/507,446, filed on Sep. 30, 2003.

(51) Int. Cl.
| | |
|---|---|
| A61K 8/00 | (2006.01) |
| A61K 8/18 | (2006.01) |
| A61K 9/14 | (2006.01) |
| A61K 31/555 | (2006.01) |
| A61Q 5/00 | (2006.01) |
| A01N 55/02 | (2006.01) |
| A61K 8/11 | (2006.01) |
| A61K 8/49 | (2006.01) |
| A61K 31/44 | (2006.01) |

(52) U.S. Cl.
CPC . *A61Q 5/006* (2013.01); *A61K 8/11* (2013.01); *A61K 8/4933* (2013.01); *A61K 31/44* (2013.01); *A61K 2800/412* (2013.01)
USPC .......................... 424/70.1; 424/489; 514/184

(58) Field of Classification Search
None
See application file for complete search history.

(56) References Cited

U.S. PATENT DOCUMENTS

| | | | | |
|---|---|---|---|---|
| 5,104,645 | A * | 4/1992 | Cardin et al. | 514/345 |
| 5,106,613 | A * | 4/1992 | Hartnett et al. | 424/70.122 |
| 5,393,519 | A * | 2/1995 | Dowell et al. | 510/119 |
| 5,674,504 | A | 10/1997 | Kauffmann | |
| 5,746,946 | A * | 5/1998 | He et al. | 252/392 |
| 5,968,528 | A * | 10/1999 | Deckner et al. | 424/401 |
| 6,406,745 | B1 * | 6/2002 | Talton | 427/213 |
| 6,491,953 | B1 * | 12/2002 | Sojka et al. | 424/490 |
| 6,544,440 | B1 * | 4/2003 | Kozasa et al. | 252/389.53 |
| 6,627,665 | B2 | 9/2003 | Waldron et al. | |
| 6,635,702 | B1 * | 10/2003 | Schmucker-Castner et al. | 524/291 |
| 6,706,258 | B1 * | 3/2004 | Gallagher et al. | 424/70.1 |
| 7,026,308 | B1 * | 4/2006 | Gavin et al. | 514/188 |
| 2003/0073749 | A1 * | 4/2003 | Waldron et al. | 516/78 |
| 2003/0108501 | A1 | 6/2003 | Hofrichter et al. | |

FOREIGN PATENT DOCUMENTS

| | | |
|---|---|---|
| CN | 1296380 A | 5/2001 |
| EP | 0376852 | 7/1990 |
| EP | 0412865 | 2/1991 |
| EP | 0863161 | 9/1998 |
| EP | 1060732 | 12/2000 |
| EP | 1080640 A1 | 3/2001 |
| JP | 200217340 | 7/2002 |
| JP | 2004512349 A | 4/2004 |
| JP | 2005504812 B2 | 2/2005 |
| JP | 11-509220 A | 3/2011 |
| WO | 0054589 * | 9/2000 |
| WO | WO 02/36086 | 5/2002 |
| WO | 03/007900 | 1/2003 |

OTHER PUBLICATIONS

Zinc Omadine® MSDS (Jul. 2003).*
Zinc-Pyrithione reference 2001.*
Man et al. Journal of the American Oil Chemists Society 1999 76:237-242.*
"Culture of fungi on cyanoacrylate skin surface strippings—a quantitative bioassay for evaluating antifungal drugs," Rurangirwa et al., Clinical and Experimental Dermatology, vol. 14, pp. 425-428 (1989).

* cited by examiner

*Primary Examiner* — Robert A Wax
*Assistant Examiner* — Caralynne Helm
(74) *Attorney, Agent, or Firm* — Miles & Stockbridge PC

(57) ABSTRACT

A composition comprising coated particles of a salt of pyrithione selected from the group consisting of monovalent and polyvalent pyrithione salts, and combinations thereof, partially or fully coated with a lipophilic agent. The composition is characterized by enhanced anti-fungal and anti-dandruff efficacy in shampoos. Also disclosed is a personal care composition, preferably a shampoo, containing a topical carrier and coated particles of a salt of pyrithione selected from the group consisting of monovalent and polyvalent pyrithione salts, and combinations thereof, partially or fully coated with a lipophilic agent.

19 Claims, No Drawings

COATED METAL PYRITHIONE PARTICLES FOR TREATMENT OF MICROORGANISMS

CROSS REFERENCE TO RELATED APPLICATIONS

This application claims priority to U.S. Provisional Application Ser. No. 60/507,446, filed on Sep. 30, 2003 that is entitled "Coated Metal Pyrithione Particles for Treatment of Microorganisms" which is incorporated by reference herein in its entirety.

FIELD OF THE INVENTION

The present invention relates to coated particles of pyrithione salts which provide improved efficacy of the pyrithione moiety through the coating, thereby enhancing the duration of antimicrobial efficacy provided by the composition. The composition is useful for providing antimicrobial, particularly antifungal efficacy when incorporated into in personal care compositions, particularly shampoos.

In shampoos, the lipophilic nature of the coating facilitates targeted delivery to the scalp, particularly sites on the scalp that contain lipophilic microorganisms, such as lipophilic yeasts, which are known to cause dandruff. Shampoos containing the coated particles of the present invention exhibit enhanced antifungal efficacy, as compared to shampoos containing uncoated particles of pyrithione salts.

BACKGROUND OF THE INVENTION

It is well known that metal pyrithiones, such as zinc and copper pyrithione, are effective antimicrobial agents. Zinc pyrithione is a well known and widely used active as an anti-dandruff and anti-fungal component of shampoos.

PCT patent application WO 03/007900 discloses the use of lipophilic agents, such as ceramides, along with zinc pyrithione to increase the level of lipids in the skin and in scalp for treatment of dandruff. However, the use of a mixture of lipids and pyrithione salts in shampoo formulations has the disadvantage that the lipids might be delivered preferentially to one locus on the scalp, and the pyrithione salts to another.

The present invention addresses that disadvantage by facilitating targeted delivery of lipids and pyrithione as a single package using a lipid coating on the pyrithione particles.

SUMMARY OF THE INVENTION

In one aspect, the present invention relates to a composition comprising coated particles of a salt of pyrithione selected from the group consisting of monovalent and polyvalent pyrithione salts, and combinations thereof, partially or fully coated with a lipophilic agent. The composition provides enhanced anti-fungal and anti-dandruff efficacy in shampoos.

In another aspect, the present invention relates to a personal care composition, preferably a shampoo, containing a topical carrier and coated particles of a salt of pyrithione selected from the group consisting of monovalent and polyvalent pyrithione salts, and combinations thereof, partially or fully coated with a lipophilic agent.

In yet another aspect, the present invention relates to a process for making an aqueous dispersion of solid zinc pyrithione particles having a solid palm oil coating on outer surfaces thereof, comprising the steps of:

(a) heating an aqueous dispersion of solid zinc pyrithione particles to an elevated temperature of from about 50 degrees Centigrade to about 80 degrees Centigrade to provide a hot aqueous dispersion, (b) heating solid palm to an elevated temperature of from about 50 degrees Centigrade to about 80 degrees Centigrade to provide liquid palm oil, and (c) admixing said liquid palm oil and said hot aqueous dispersion to provide a mixture, and cooling the mixture to provide said aqueous dispersion of solid zinc pyrithione particles having said solid palm oil coating. The resulting dispersion suitably coated zinc pyrithione particles in an amount of between about 40% and about 50% based upon the total weight of the dispersion.

In still another aspect, the present invention relates to an aqueous antimicrobial dispersion concentrate comprising water and from about 25% to about 50% by weight of solid particles of a pyrithione salt, based upon the weight of the dispersion. The solid particles of the pyrithione salt are coated particles having a lipophilic coating on the outer surfaces thereof. The coated particles exhibit an antimicrobial efficacy improvement on a comparative corneofungimetry bioassay test of at least 25% as compared to the antimicrobial efficacy of a dispersion of uncoated particles of said pyrithione salt on said bioassay test. Another aspect relates to a personal care composition comprising a topical carrier and from about 0.5% to about 5% of this concentrate, based upon the total weight of the personal care composition. The personal care composition exhibits an antimicrobial efficacy improvement on a comparative corneofungimetry bioassay test of at least 15% as compared to the antimicrobial efficacy on said bioassay test of a personal care composition containing an identical amount of a dispersion of uncoated particles of said pyrithione salt.

These and other aspects will become apparent upon reading the following detailed description of the invention.

DETAILED DESCRIPTION OF THE INVENTION

It has now been surprisingly found that coated pyrithione particles containing a lipophilic fatty oil coating provides an effective vehicle for delivering the pyrithione to desirable lipophilic sites on the scalp. At these sites, lipophilic microorganisms, such as the lipophilic *Malassezia* sp yeasts, which are known to cause dandruff, are likely to be found. Targeted delivery to these sites enhances the anti-fungal and anti-dandruff efficacy of shampoos containing these coated pyrithione particles, as compared to shampoos containing uncoated pyrithione particles.

The pyrithione salt employed in the present invention is preferably selected from the group consisting of zinc, copper, silver, zirconium salts, and combinations thereof. The more preferred pyrithione salt is selected from zinc and copper salts, most preferably the zinc salt. The zinc salt is suitably used in the form of a particulate dispersion, slurry or powder. The zinc pyrithione may be used in any particle form including, for example, crystalline form such as platelets, rods, needles, blocks, round and amorphous, regularly, or irregularly shaped particles. The average particle diameter of the zinc pyrithione particles (maximum dimension) is typically from about 0.1 to about 50 µm, preferably from about 0.1 m to about 10 µm, more preferably from about 0.1 µm to about 5 µm as determined, for example, using Horiba LA-910 Laser scattering particle size distribution analyzer.

The lipophilic coating on the coated particles of the present invention comprises a synthetic or natural fatty oil that is solid or liquid at room temperature. Thus the term "lipophilic agent" as used herein is intended to encompass both oils and waxes. The fatty oil comprises fatty acids or fatty acid esters having a number average molecular weight within the range of about 150 to about 1500, and a number of carbons within the range of 8 to 22, or mixtures thereof. The fatty acid esters can comprise mono-, di- or tri-glycerides, or mixtures thereof. The preferred coating material is palm oil.

The lipophilic coating component preferably comprises greater than 0.01% by weight, preferably greater than 1%, more preferably greater than 3%, based upon the total weight of the coated pyrithione particles. Typically, the content of the lipophilic agent in the coated particles are the range of about 3-15%. In a shampoo containing 1% by weight of zinc pyrithione, the amount of the lipophilic coating agent is generally from about 0.001% to about 0.15% by weight, preferably from about 0.01 to about 0.15%, more preferably from about 0.03 to about 0.15%, based upon the weight of the shampoo.

Suitable fatty acids and fatty acid esters include hydrocarbon oils, waxes, di- and tri-glyceride oils include, for example, hydrogenated and non-hydrogenated polyalkenes oils, hydrogenated oils, polyethylene and polybutene palm oil, caster oil, soyabean oil, derivatized soy bean oils, sunflower oil, cotton seed oil, corn oil, walnut oil, peanut oil, sesame oil, vegetable oil, vegetable oil derivatives, coconut oil, coconut oil derivatives.

The fatty acids/fatty acid esters can be naturally occurring, or derivatives thereof. The carbon chain length of the coating is generally between C8 and C22, and includes mixtures thereof. The fatty acids can be saturated and unsaturated, linear and branched chain fatty acids. They are selected based on the chemical and physical properties of fatty acids and their derivatives there from.

Suitable natural and synthetic sources of fatty acids, and their derivatives, include those of animal and vegetable origin, such as lanolin oil, fish oils, animal oils, coconut oil, palm oil, butter fat, soyabean oil, sunflower oil, cotton seed oil, corn oil and mixture thereof. Preferred fatty acid sources are palm oil, partially and fully hydrogenated fatty oils, fatty acids, such as those hydrogenated soyabean oil, palm oil, palmkernel oils, fish oil, polyol fatty acid esters.

In one alternative, the lipophilic coating agent is solid at room temperature, becomes liquid at an elevated temperature, and forms a film upon cooling. Desirably, solid coating material can become a liquid at around 40-100° C., and then form a film while cooling. Alternatively, the lipophilic coating agent is suitably solvent soluble, and forms a film when it is dry. Illustratively, the coating agent is suitably dissolved in an organic solvent such as alkyl alcohols, like methanol and ethanol, acetone, ethers, halogenated hydrocarbons and aromatic solvents, and then form film while the solvent is evaporated.

Particle coating in water in the present invention involves coating of a metal pyrithione or a polyvalent salt of a pyrithione particles in a slurry or suspension form in the presence of a coating material under conditions that the coating material either in a liquid form, or in solution. The coated particle size, shape and thickness depend upon the original particle size and shape in the slurry or suspension, temperature, and amount of the coating material employed. The process can be simply described as addition of coating material in liquid form (desirably at a melt point temperature below about 90 Centigrade) into the slurry or suspension at the temperature the coating material is in its liquid form with a suitable stirring rate followed by cooling, or heating a mixture of metal pyrithione slurry and a coating component or mixtures of coating materials at a highest melt point temperature of the coating material employed followed by cooling.

Particle coating in organic solvent involves addition of a metal pyrithione or a polyvalent salt of a pyrithione powder to a solution of coating material(s) in an organic solvent at room or higher temperature, followed evaporation of the solvent at stirring. The coated particle size, shape and thickness are depended on the original particle size, and shape of the metal pyrithione, and amount and properties of the coating material.

Powder coating can also suitably be used to coat the pyrithione at or above the melt point of the polymeric coating material. The liquid coating material forms a film or a coating layer on the particles while cooling. The coated particle size, shape and thickness of the coating are dependent on the original size and shape of the metal pyrithione particle, and on the amount and properties of the coating material used. This process is particularly suitable for coating particles with materials having a low melt point (preferably below about 90 C).

The coated pyrithione particles of the present invention are suitably employed in personal care compositions containing a topical carrier. The topical carrier is suitably selected from a broad range of traditional personal care carriers depending on the type of composition to be formed. By suitable selections of compatible carriers, it is contemplated that the present anti-microbial compositions may be prepared in the form of daily skin or hair products such as hair rinses, daily hair-grooming products, such as hair lotions, hair sprays, hair tonics, conditioning treatments and dressings, and the like, or they may be prepared in the form of cleansing products, such as hair and/or scalp shampoos.

The topical carrier in liquid hair compositions may be water, common organic solvents, or mixtures thereof. Suitable common organic solvents are C2-C3 alkyl alcohols such as ethanol, propanol, isopropanol, glycerine. Other solvents such as fatty alcohols and esters can also be used.

The anti-microbial compositions of the present invention may be aqueous systems which comprise from about 40% to about 92%, preferably from about 50% to about 85%, more preferably from about 60% to about 80%, water by weight of the compositions.

When the compositions of the present invention are an anti-dandruff shampoo, the pH of the compositions ranges, in general, from about 2 to about 10, preferably from about 3 to about 9, more preferably from about 4 to about 8, most preferably from about 5.5 to about 7.5.

The following example is intended to illustrate, but in no way limit, the scope of the present invention. All coated particles were characterized by ESCA, SEM, and particle size distribution analyzer, and the content of zinc pyrithione in the coated particles was determined using a standard titration method.

EXAMPLE 1

Zinc pyrithione powder (approx 200 grams) having a median particle size of about 3.4 microns was placed in a small granulator. The palm oil (approx 24 g) was made molten on a hot plate and placed in a heated feed vessel where it was maintained at 70° C. A 2-fluid nozzle was heat traced and maintained at 75° C. The granulator was started and the molten coating material sprayed into the churning powder. The coated particles were characterized as follows:
Zinc pyrithione assay: 85.8%
Particle size (Horriba LA-910): median ($D_{50}$): 7.44 µm; Sp. Area: 17647 $cm^2/Cm^3$ after 2 min sonication.

ESCA analyses of atomic concentrations and the coating thickness derived from the attenuation of the Zn and S signals indicated that the presence of the coating was 35 Å. SEM images of the coated particles showed that the particles are visibly coated with cluster features.

COMPARATIVE EXAMPLE A

To a stirring suspension of 210.0 g 48.0% zinc pyrithione (median particle size of 0.47 μm) in 150 ml D.I. water at ~65° C. was slowly added hot liquid oil consisting 4.1 g stearyldimethicone at 60-65° C. After stirring at 500 RPM for 10 min at this temperature, the dispersion was gradually cooled down to room temperature with a stirring speed of 300 RPM.

The coated particles were characterized as follows:
Zinc pyrithione assay: 32.0%
Particle size (Horriba LA-910): median ($D_{50}$): 0.478 μm; Mean: 0.507 μm; Sp. Area: 136981 $cm^2/cm^3$ after 2 min. sonication.

ESCA analyses of atomic concentrations and the coating thickness derived from the attenuation of the Zn and S signals indicated that the presence of the coating was 15 Å as shown in Table 1. SEM images of the coated particles showed that the particles are thinly coated. The zinc pyrithione particles (0.1-1 μm, mix of blocks and platelets) were well defined with some scattered patches of coating, and the edges of the particles were softened in appearance. It is possible that these coating-related features having curved rather than straight or angular character as would be seen for fine zinc pyrithione particles may be part of the original fine particles and just may be thin coating as seen in ESCA.

The coated particles showed activity in a qualitative Zone of Inhibition (ZOI) test against *Malassezia furfur*, demonstrating that the coating did not prevent the migration of zinc pyrithione through agar.

COMPARATIVE EXAMPLES B-D

Following the procedure of Example 1—Part (I), zinc pyrithione particles in suspension of 48.0% zinc pyrithione (median particle size of 0.47 μm) were coated in-situ with aminofunctional polydimethylsiloxane (Amodimethicone, Dow Corning 2-8566 Amino Fluid, Example B), lecithin (Centromix LP 250, Example C) and bis-PEG-12 dimethicone Beeswax (siliconyl beeswax, Example D). The characterization data of these coated zinc pyrithione particles are tabulated in Table 1.

TABLE 1

Characterization data of Comparative Examples A–C

| | Example B with Amodimethicone | Example C with lecithin | Example D with siliconyl Beeswax |
|---|---|---|---|
| Coating content (%) | 7.5 | 3 | 3 |
| Coating thickness (Å) | — | 35 | 33 |
| Particle size ($D_{50}$, μm) | 13.41 | 0.46 | 0.49 |

In initial performance testing, Example 1 and the and Comparative Examples all showed coated particle antimicrobial activity in a qualitative Zone of Inhibition (ZOI) test against *Malassezia furfur*, demonstrating that the coating did not prevent the migration of zinc pyrithione.

As a more advanced test, "corneofungimetry" was used to evaluate the particles prepared in accordance with the Example and Comparative Examples. This test is a good pre-clinical screening method because it requires growing the *Malassezia furfur* sp on a substrate that is more representative of its natural environment. Cyanoacrylate is used to harvest a layer of skin, and these skin surface strippings are treated with olive oil to simulate sebum. The prepared skin samples are then treated with the actives under investigation, inoculated with the microorganism of interest and incubated. In this study the actives were the coated zinc pyrithione particles and the test organism used was *Malassezia furfur*. The relative efficacy of the treatments is determined by looking for inhibition of growth compared to the controls and this data was collected using computerized image analysis and vital staining. It shows the coated zinc pyrithione to be more efficacious against *Malassezia furfur* than the uncoated material. It was used to test the zinc pyrithione efficacy both as 1% aqueous dispersion and at 1% in a shampoo formulation. The formulated shampoo, for which test results are provided in Table 3 below, contained the following components: STEPANOL AM-V anionic surfactant, 68.3%; STEPAN SAB-2 suspending agent, 5%; NINOL 40-CO non-ionic foaming agent, 2%; coated zinc pyrithione particles, 1% based on the pyrithione content; GLYDANT preservative, 0.3%; deionized water providing the balance of 100%; all weight percents being based upon the total weight of the shampoo.

The corneofungimetry bioassay was performed on normal stratum corneum harvested from 20 healthy volunteers using cyanoacrylate adhesive. Samples were dipped into olive oil and stored in a sterile environment for 3 days. The stratum corneum samples impregnated by olive oil were dipped in a second step in the 1% suspension of zinc pyrithione in water or in shampoos containing 1% zinc pyrithione. Additional information on the "corneofungimetry" test is available in a technical journal article entitled "Culture of fungi on cyanoacrylate skin surface strippings—a quantitative bioassay for evaluating antifungal drugs." By A. Rurangirwa, C. Peirard-Franchimont and G. E. Pierard C appearing in Clinical and Experimental Dermatology (1989) Volume 14, pages 425-428.

*Malassezia furfur* was cultured on MLNA (Modified Leeming and Notman Agar) medium. Suspensions of fungal cells were prepared in physiologic saline ($10^4$-$10^5$ cells/ml). Aliquots of 250 μl of these suspensions were deposited onto the stratum corneum samples and incubated under moist conditions at 27° C. for 9 days. Samples were then stained using neutral red as a vital stain identifying living fungi growing on the human stratum corneum. The number of positive fungal cells was counted by $mm^2$ using computerized image analysis (Analysis Olympus). The medians and ranges were determined. Between-product comparisons were performed using the paired non-parametric Friedman test followed by the Dunn test.

The data shown in Table 2 and 3 demonstrated that the samples coated with 11.7% palm oil (Example 1) provided the best percent antifungal efficacy results. In comparison, 4.0% stearyl dimethicone (Comparative Example A) showed modest efficacy improvements over the uncoated controls in both water dispersion and in the formulated shampoos, while the sample coated 7.5% aminosilicone (Comparative Example B) shows some good efficacy improvement in water suspension, but a little in the formulated shampoo. Surprisingly, the samples coated with lecithin (Comparative Example C) and siliconyl beeswax (Comparative Example D) show negative efficacy improvement in water suspensions.

TABLE 2

Comparative corneofungimetry bioassay test result of the coated samples in water suspensions

|  | Physiologic saline | Uncoated | Example A | 1 | B | C | D |
|---|---|---|---|---|---|---|---|
| Coating material (%) | 0 | 0 | 4.0 | 11.7 | 7.5 | 3.0 | 3.0 |
| Median positive fungal cells# from 20 samples | 810 | 451 | 433 | 339 | 372 | 585 | 515 |
| % killing compared to saline control | 0 | 44 | 47 | 58 | 54 | 28 | 36 |
| Efficacy improvement over uncoated control (%) | — | — | 7 | 32 | 23 | −36 | −18 |

TABLE 3

Comparative corneofungimetry bioassay test result of the coated samples in formulated shampoos

|  | Physiologic saline | Uncoated (Control) | Example A | Example 1 | Example B |
|---|---|---|---|---|---|
| Coating material (%) | — | — | 4.0 | 11.7 | 7.5 |
| Median positive fungal cells# from 20 samples | 756 | 363 | 326 | 286 | 353 |
| % killing compared to saline control | 0 | 52 | 57 | 62 | 53 |
| Efficacy improvement over uncoated control (%) | — | — | 10 | 19 | 2 |

While the invention has been described above with reference to specific embodiments thereof, it is apparent that many changes, modifications, and variations can be made without departing from the inventive concept disclosed herein. Accordingly, it is intended to embrace all such changes, modifications and variations that fall within the spirit and broad scope of the appended claims. All patent applications, patents and other publications cited herein are incorporated by reference in their entirety.

What is claimed is:

1. A shampoo composition comprising:
   a zinc pyrithione particle coated with palm oil, wherein the palm oil coating is from about 0.01% to about 15% by weight of the coated particle; and
   water or an organic solvent.

2. A shampoo composition comprising particles of a zinc salt of pyrithione coated with a lipophilic agent; wherein said lipophilic agent coating is from about 0.01% to about 15% by weight of the coated particle; and wherein the lipophilic agent is selected from one or more of the group consisting of petrolatum, mineral oil wax, hydrogenated and non-hydrogenated polyalkene, hydrogenated oil, paraffin, synthetic paraffin, polyethylene palm oil, polybutylene palm oil, castor oil, soya bean oil, sunflower oil, cotton seed oil, corn oil, walnut oil, peanut oil, sesame oil, vegetable oil, and coconut oil.

3. The shampoo composition of claim 2, wherein said zinc salt of pyrithione is present in said coated particles in a weight percent of between about 85% to about 99% based upon the weight of the coated particles.

4. The shampoo composition of claim 2, wherein the lipophilic agent is present in said coated particles in a weight percent between about 3% and about 15%, based upon the weight of the coated particles.

5. The shampoo composition of claim 2 wherein said coated particles are individually fully coated on the surface thereof by said lipophilic agent.

6. The shampoo composition of claim 2, further comprising an organic solvent, with the proviso that said lipophilic agent is insoluble in said organic solvent.

7. The shampoo composition of claim 2, further comprising.

8. The shampoo composition of claim 6 wherein said organic solvent is selected from a group consisting of methanol, ethanol, acetone, ethers, halogenated hydrocarbons, and aromatic solvents.

9. The shampoo composition of claim 2 wherein said coated particles comprise a coating having a thickness of between 10 and 100 Angstroms.

10. A shampoo composition comprising:
    a zinc pyrithione particle coated with palm oil, wherein the palm oil coating is from about 0.01% to about 15 % by weight of the coated particle, wherein the coated zinc pyrithione particle is present in an amount of about 1% based on the total weight of the shampoo composition, and wherein the coated zinc pyrithione particle has a median particle size of 7.44 microns;
    an anionic surfactant, wherein the anionic surfactant is present in an amount of about 68.3% based on the total weight of the shampoo composition; a suspending agent, wherein the suspending surfactant is present in an amount of about 5% based on the total weight of the shampoo composition;
    non-ionic foaming agent, wherein the foaming agent is present in an amount of about 2% based on the total weight of the shampoo composition; and
    de-ionized water.

11. The shampoo of claim 2, wherein the lipophilic agent comprises a fatty oil.

12. The shampoo of claim 2, wherein the average particle diameter of the particles is about 0.1 to about 50 microns.

13. The shampoo of claim 2, wherein the average particle diameter of the particles is about 0.1 to about 10 microns.

14. The shampoo of claim 2, wherein the lipophilic agent comprises one or more fatty acid or fatty acid esters having a number average molecular weight within the range of about 150 to about 1,500 and a number of carbons within the range of 8 to 22.

15. The shampoo of claim 2, wherein the lipophilic agent comprises one or more mono-, di-, or triglycerides.

16. The shampoo of claim 2, wherein the coating consists of more than one lipophilic agents.

17. The shampoo of claim 2, wherein the coating consists of palm oil.

18. The shampoo of claim 2, exhibiting an antimicrobial efficacy improvement on a comparative corneofungimetry bioassay test of at least 15%, as compared to the antimicrobial efficacy on said bioassay test of a shampoo composition containing an identical amount of a dispersion of uncoated particles of said pyrithione salt.

19. The shampoo as claim in claim 2, wherein the coated particles exhibit an antimicrobial efficacy improvement on a comparative corneofungimetry bioassay test of at least 25%, as compared to the antimicrobial efficacy of a dispersion of uncoated particles of said pyrithione salt on said bioassay test.

* * * * *